United States Patent [19]

Haake

[11] Patent Number: 6,140,083
[45] Date of Patent: Oct. 31, 2000

[54] LEPTOSPIRAL OUTER MEMBRANE PROTEIN, LIPL46

[75] Inventor: David A. Haake, Culver City, Calif.

[73] Assignee: The Regents of the University of California, Oakland, Calif.

[21] Appl. No.: 09/122,210

[22] Filed: Jul. 23, 1998

[51] Int. Cl.[7] .................................................. C12P 21/06
[52] U.S. Cl. .................. 435/69.3; 435/252.3; 435/320.1; 536/23.1; 536/23.7; 530/350
[58] Field of Search ................. 536/23.1, 23.7; 435/252.3, 69.3, 320.1, 325; 530/350

[56] References Cited

U.S. PATENT DOCUMENTS

| | | | |
|---|---|---|---|
| 4,366,246 | 12/1982 | Riggs .......................................... | 435/68 |
| 4,474,893 | 10/1984 | Reading .................................... | 436/547 |
| 4,676,980 | 6/1987 | Segal et al. ............................... | 424/85 |
| 5,091,301 | 2/1992 | Zuerner ..................................... | 435/6 |
| 5,397,698 | 3/1995 | Goodman et al. ......................... | 435/6 |
| 5,401,631 | 3/1995 | Lane et al. ................................. | 435/6 |
| 5,466,577 | 11/1995 | Weisburg ................................... | 435/6 |
| 5,516,641 | 5/1996 | Ullman et al. ........................... | 435/91.1 |
| 5,643,754 | 7/1997 | Haake .................................... | 435/69.3 |
| 5,658,757 | 8/1997 | Haake et al. ........................... | 435/69.1 |
| 5,824,321 | 10/1998 | Haake et al. ........................... | 424/266.1 |

FOREIGN PATENT DOCUMENTS

| | | |
|---|---|---|
| WO 95/32220 | 11/1995 | WIPO . |
| WO 97/26274 | 1/1996 | WIPO . |
| WO 96/36355 | 11/1996 | WIPO . |

OTHER PUBLICATIONS

Blanchard–Channell, et al., Infection and Immunity, No. 8, 59:2790–2798, Aug. 1991, Characterization of *Borrelia coriaseae* Antigens with Monoclonal Antibodies.

Allan, et al. Infection and Immunity, No. 3, 45:637–641, Sep. 1984, Molecular Cloning of the Major Outer Membrane Protein of *Chlamydia Trachamatis*.

Haake, et al., Infection and Immunity, No. 3, 59:1131–1140m, Mar. 1991, "Changes in the Surface of *Leptospira Interrogans* Serovar Grippotyphosa during in Vitro Cultivation".

Zuerner, et al., Microbial Pathogenesis, 10:311–322, 1991, Characterization of outer membrane and secreted proteins of *Leptospira serovar* pomona.

Van Eys et al., "DNA Hybridization . . . Leptospira.", J Gen. Microbiol. 134:567–574 (Mar. 1998).

Yasuda et al., "Doxyribonucleic Acid Relatedness Between Serograys and serovan in the family Leptospiraceae . . ."Int. J. SN Bact. 37(4):407–415 (Oct. 1987).

Bolin, C.A., et al., "Effect of vaccination with a pentavalent leptospiral vaccine on *Leptospira interrogans* serovar hardjo type hardjo–bovis infection of pregnant cattle", Am.J.Vet. Res., 50:161 (1989).

Bolin, C.A., et al., "Effect of vaccination with a pentavalent leptospiral vaccine containing *leptospira interrogans* serovar hardjo type hardjo–bovis on type hardjo–bovis infection of cattle", Am.J. Vet. Res., 50:2004 (1989).

Bolin, C.A., "effect of vaccination with a monovalent *leptospira interrogans* serovar hardjo type hardjo–bovis vaccine on type hardjo–bovis infection of cattle", et al., Am. J. Vet. Res., 52:1639–1643 (1991).

Brandt, et al., "Immunogenic Integral Mambrane Proteins of *Borrelia burgdorferi* Are lipoproteins", Infect. Immun. 58:983–991 (1990).

Chamberlain, N.R., et al., "Major Integral Membrane Protein Immunogens of *Treponema pallidum* Are proteolipids", Infect. Immun., 57:2872–2877 (1989).

Cunningham, et al., "Selective Release of the *Treponema pallidum* Outer membrane and Associated Polypeptides with Triton X–144", J. Bacteriol., 170:5789–5796 (1988).

Doherty, J.P., et al., "Expression of two conserved leptospiral antigens in *Escherichia coli*", J. Med. Microbiol, 28:143–149 (1989).

Farr, R.W., "Leptospirosis", State–Of–The–Art Clinical Article, Clinical infectious Diseases, 21:1 (1995).

Haake, D.A., et al., "Molecular Cloning and Sequence Analysis of the Gene Encoding OmpL 1, a Transmembrane Outer Membrane Protein of Pathogenic Leptospira spp.", J. Bacteriol., 175(13):4225–4234 (Jul. 1993).

Hayashi, S., et al., Lipoproteins in Bacteria, J. Bioenerg. Biomembr., 22:451 (1990).

Miyamoto, M., et al., "molecular Cloning and Sequence Analysis of Antigen Gen tdpA of *Treponema denticola*", Infect. Immun., 59:1941–1947 (1991).

Ramadass, P., et al, "Genetic Characterizationof pathogenic Species by DNA Hybridization", Int'l J. Of Systematic Bacteriol., 42:215–219 (1992).

Stamm, et al., "Changes in the Cell Surface Properties of *Treponema pallidum* That occur during in Vitro Incubation of Freshly Extracted Organisms", Infec. Immun. 55:2255–2261 (1987).

Thiermann, et al., "Leptospirosis: Current Developments and trends", J. Am. Vet. Med. Assoc., 184:722(1984).

Thomas, W., et al., "Molecular Cloning, Expression, and DNA Sequence Analysis of the Genes That Enclodes the 16–Kilodalton Outer Membrance Lipoprotein of *Serpulina hyodysenteriae*", Infect. Immun., 61–1136 (1993).

Van Eys, G.J.J.M., et al., "DNA Hybridization with Hardjobovis–specific Recombinant Probes as a Method for Type Discrimination of *Leptospira interrogans* Serovar hardjo", J. Of Gen. Microbiology, 134:567 (1988).

(List continued on next page.)

*Primary Examiner*—Jeffrey Stucker
*Attorney, Agent, or Firm*—Gray Cary Ware & Freidenrich LLP; Lisa A. Haile

[57] ABSTRACT

An antigenic preparation is provided containing an outer membrane protein associated with pathogenic strains of Leptospira. The protein has been designated "LipL46" for "lipoprotein from Leptospira" and because the isolated polypeptide migrates to a position corresponding to a molecular weight of 46 kD in a denaturing polyacrylamide gel. The invention provides polynucleotides encoding LipL46 and antibodies that bind the protein which are useful in the diagnosis of leptospirosis. In addition, LipL46 can be used immunologically as a vaccine for spirochete-associated pathologies.

14 Claims, 4 Drawing Sheets

OTHER PUBLICATIONS

Cinco, M., et al., "Immunodominant antigens recognized by the human immune response to infection by organisms of the species *Leptospira interrogans* serogroup Australis", FEMS Microbiology Letters, 89:287–298 (1992).

Brown, et al., "Protein and Antigen Profiles of Prevalent Serovars of *Leptospira interrogans*", Infection and Immunity, vol. 59., No. 5, pp. 1772–1777, issued May, 1991.

Gitton, et al., Immunoblotting study of the antigenic relationships among eight serogroups of Leptospira, Veterinary Microbiology, vol. 32, issued 1992, pp. 293–303.

Nicholson, Vivian and Prescott, John, Outer Membrane proteins of three pathogenic Leptospira species, Veterinary microbiology, 36, pp. 123–138, (1993).

Nunes–Edwards, et al., Identification and Characterization of the Protein Antigens of *Leptospira interrogans* serovar hardjo, Infection and Immunity, vol. 48, No. 2, pp. 492–497, May 1985.

Auran, et al., "Isolation of the Outer Sheath of Leptospira and its Immunogenic Properties in Hamsters", Infect. Immun., 5:968–975 (1972).

Bey, R.F., et al., "Immunognicity of Whole Cell and Outer Envelope Leptospiral Vaccines in Hamsters", Infect. Immun., 10:1051–1056 (1974).

Blanco, et al., "Isolation of the Outer Membranes from *Treponema pallidum* and *Treponema vincenti*", J. Bateriol., 176:6088–6099 (1994).

Holt, S.C., "Anatomy and Chemistry of Spirochetes", Microbiol. Rev., 42:114–160 (1978).

Osborn, et al., "Mechanism of Assembly of the Outer Membrane of *Salmonella typhimurium*", J. Biol. Chem., 247:3962–3972 (1972).

Penn, et al., "The Outer Membrane of *Treponema pallidum*: Biological Significance and Biochemical Properties", J. Gen. Microbiol., 131:2349–2357 (1985).

Radolf, et al., "Characterization of Outer Membranes Isolated from *Borrelia burgdorferi*, the Lyme Desease Spirochete", Infect. Immun., 63:2154–2163 (1995).

Radolf, et al., "Characterization of Outer Membrances Isolated from *Treponema pallidum*, the Syphilis Spirochete", Infect. Immun. 63:4244–4252 (1995).

Shang, E.S. et al., "The Rare Outer Membrane Protein, OmpL1, of Pathogenic Leptospira Species is a Heat–Modifiable Porin", Infect. Immun. 63(8):3174–3181 (1995).

Shang, E.S., et al., "Molecular Cloning and Sequence Analysis of the Gene Encoding LipL41, and Surface–Exposes Lipoprotein of Pathogenic Leptospira Species", Infect. Immun. 64:2322–2330 (1996).

Weigel, L.M., et al., "The 47–kDa major lipoprotein immunogen of *Treponema pallidum* is a penicillin–binding protein with carboxypeptidase activity", Proc. Natl. Acad. Sci. USA, 91:11611–11615 (1994).

Champion, et al., Infect. Immun 62(7):2653–2661 (Jul. 1994).

```
1   .TCAGTTGTAACTTATACGTAACTCCCTCCCTCTATCTTTGTTCAACCTTCTACGG..TATTTTCAAGGAGTATAAA
          CRF1 STOP                                                    RBS

80  ATG AAA TCA ACT TTC CTA CAA AGG GCT TTG CTT TTA ATC GTA AGT GCC GCC TTA TTA CTT
    Met Lys Ser Thr Phe Leu Gln Arg Ala Leu Leu Leu Ile Val Ser Ala Ala Leu Leu Leu

140 TCT TCT TTT ATC AAT TGT AAA GAA GAC AAA GAC AAT AGT ATG TTG CTT CTT GCT
    Ser Ser Phe Ile Asn Cys Lys Glu Asp Lys Asp Asn Ser Met Leu Leu Leu Ala

200 CTC TTA TCG GGA AAT AGC GAC GCC GGA GCT ATC TGC GAC GGT GCT TCC GTT CAA
    Leu Leu Ser Gly Gly Asn Ser Asp Ala Gly Ala Ile Cys Asp Gly Ala Ser Val Gln

260 GGT GGA AAC ACG GTT CTT TCG GGT AAC ATA ACT TCT CAA AAT CTT TCC GCC TAC TCT
    Gly Gly Asn Thr Val Leu Ser Gly Asn Ile Thr Ser Gln Asn Leu Ser Ala Tyr Ser

320 TCT TCT TCG TTA AGT GGA ATT GTT AGA GTT ACT GCT GGT TCC TTA ATC TTT GAA AGA
    Ser Ser Ser Leu Ser Gly Ile Val Arg Val Thr Ala Gly Ser Leu Ile Phe Glu Arg

380 GGT TCT GTA ATT TTC GGA ACT GCT ATC TTC GGA ACT GAA CAA GGA GGA AAG ATC
    Gly Ser Val Ile Phe Gly Thr Ala Ile Phe Gly Ser Ala Leu Ile Gly Gln Gly Lys Ile

440 GTT ACA AAC GGA GAC GCT GCC GCA CCC GTA TGC TTT ACT TCT TCT AAA GTT TCC GGA AAC
    Val Thr Asn Gly Asp Ala Ala Ala Pro Val Cys Phe Thr Ser Ser Lys Val Ser Gly Asn
```

FIG. 1A

```
500  AGA GCC CCA GGC GAT TGG GGT GGT ATC TTG ATC GTA GGA GAC GGT ATT GGT TCC AGA GCA
     Arg Ala Pro Gly Asp Trp Gly Gly Ile Leu Ile Val Gly Asp Gly Ile Gly Ser Arg Ala

560  GCC GCA CAA AAC ACG GAA GGT GGA ACC GGT CTT CAA TAC AAT AGC GGT AAT GAT AAC
     Ala Ala Gln Asn Thr Glu Gly Gly Thr Gly Leu Gln Tyr Asn Ser Gly Asn Asp Asn

620  GGA AGT TCG GGT AAC CTT ACT TAT ACG ATC GTT GAA TTT GCC GGA AAC GAA GTT TCT CCC
     Gly Ser Ser Gly Asn Leu Thr Tyr Thr Ile Val Glu Phe Ala Gly Asn Glu Val Ser Pro

680  GGT GAC GAG TTA AAC GGA CTT ATG TCT GTA GGA AGT GGT ACT ACT TTA GAT CAC
     Gly Asp Glu Leu Asn Gly Leu Met Ser Val Val Gly Ser Gly Thr Thr Leu Asp His

740  GTT CAA GTC CAC AGA CAT TTG GAC GAC GGT ATA GAA GCT TGG GGC GCT TGC ACT GGT
     Val Gln Val His Arg His Leu Asp Asp Gly Ile Glu Ala Trp Gly Gly Ala Trp Thr Gly

800  AAA TAT CTT TTG ATG ACC GGT GGA ATG GAC GAC GAT TTA GAT GAA GCT TTC ACT
     Lys Tyr Leu Leu Met Thr Gly Gly Met Asp Asp Asp Leu Asp Glu Ala Phe Thr

860  GGA AAA GTT CAG TTC CAT AAA TAT CCT ACT AGT TGT GGA ACC GCA TCC
     Gly Lys Val Gln Phe His Lys Tyr Pro Thr Ser Cys Gly Gly Thr Ala Ser

920  ACC GAC CCA CAC GGT TTT GAA ATG GAC GGA ACT CAT AGC GGT GGT ACC GCA TCC GCG ACT
     Thr Asp Pro his Gly Phe Glu Met Asp Gly Thr His Ser Gly Gly Thr Ala Ser Ala Thr
```

FIG. 1B

```
980   TCT AAA ACG GCC ACA AAC GTA AAA CTT TCC AAC TTT ACT CTT CTT GGA AAA AGC GTT TCC
      Ser Lys Thr Ala Thr Asn Val Lys Leu Ser Asn Phe Thr Leu Leu Gly Lys Ser Val Ser

1040  AAC GGA TTT GGA GCA AGA CTG AGA CTT ATT CAA GGA CTT AAA GGT TCG AAC GGA GCC ATT
      Asn Gly Phe Gly Ala Arg Leu Arg Leu Ile Gln Gly Leu Lys Gly Ser Asn Gly Ala Ile

1100  TAC GGT TTT CAA GCC GGA AAC GTT GAT TGT GTA GCG AAT GCA AGC GTA GGT GGT CCA GTG
      Tyr Gly Phe Gln Ala Gly Asn Val Asp Cys Val Ala Asn Ala Ser Val Gly Gly Pro Val

1160  ACC TCT CCT ACT TTT GCA AAC GTC TTA GTA GAA GCT TCT AAA GGA AAC GGA AAT ACC GCG
      Thr Ser Pro Thr Phe Ala Asn Val Leu Val Glu Ala Ser Lys Gly Asn Gly Asn Thr Ala

1220  GCT TGT TCG TTA CCT ACA AAC GGA CTT TCT TCC ACT CCT GTA ATT CCT TTA GGT TCT GGG
      Ala Cys Ser Leu Pro Thr Asn Gly Leu Ser Ser Thr Pro Val Ile Pro Leu Gly Ser Gly

1280  GAT TCG GAT AAC TGC GAA TTT GCG ACC AAA CCG GAT TAT CAA CCT TCT GGA GAA GCC GCG
      Asp Ser Asp Asn Cys Glu Phe Ala Thr Lys Pro Asp Tyr Gln Pro Ser Gly Glu Ala Ala

1340  GCT TTA GCC GGT TCC CGT CTA AGC GCT CAA TCC TCG GAT TCG TTT TTT ACC GAT AAC ACC
      Ala Leu Ala Gly Ser Arg Leu Ser Ala Gln Ser Ser Asp Ser Phe Phe Thr Asp Asn Thr

1400  ACT TAC GGC GGT ATG GTA AAC GGT TTG AAC TGG GCT TTC GGT TGG ACC GTT TAT AGA GCA
      Thr Tyr Gly Gly Met Val Asn Gly Leu Asn Trp Ala Phe Gly Trp Thr Val Tyr Arg Ala

1460  AGA TAA ACTTATACATTAGGATTCCCTAATTGGGAATCCTAATTCAAAATTTTAATCTATTTTAAAATCATTAGA  (SEQ ID NO:1)
      Arg *                                                                           (SEQ ID NO:2)
                               <------------
           ------------>
```

FIG. 1C

LEPTOSPIRAL OUTER MEMBRANE PROTEIN, LIPL46

This invention was made with Government support under Grant No. AI34431, awarded by the National Institute of Health. The Government has certain rights in this invention.

TECHNICAL FIELD

This invention relates generally to antigenic preparations and more specifically to a Leptospira outer membrane protein (LipL46) which is useful for inducing a protective immune response in a subject.

BACKGROUND

Spirochetes are helically shaped, motile bacteria. Among the spirochetes, four genera are identified as pathogens, Treponema, Borrelia, Serpulina and Leptospira. The treponemes include *Treponema pallidum,* the causative agent of the venereal disease syphilis in humans. Other treponemes such as *T. denticola* and *T. vincentii* are usually found in the mouth and have been linked to periodontal disease. Several other spirochetes can cause animal as well as human disease. *Borrelia recurrentis,* which is carried by ticks, causes relapsing fever in which the infected subject suffers repeated bouts of fever and chills. *B. burgdorferi,* also tick-borne, is responsible for Lyme disease, a debilitating ailment known to cause arthritis, loss of myelin from nerve cells and myocarditis. *Serpulina hyodynsenteriae* causes outbreaks of diarrhea and weight loss in pigs. *Serpulina pilosicoli* has recently been identified as a cause of chronic diarrhea in humans. Pathogenic strains of Leptospira frequently cause the zoonotic disease, leptospirosis, and are capable of infecting most mammalian species. At present, there are seven pathogenic species and three nonpathogenic species within the genus Leptospira. Infection occurs either through direct contact with an infected animal or indirect contact with contaminated soil or water. In livestock, the disease causes economic losses due to abortion, stillbirth, infertility, decreased milk production, and death.

Efforts to control leptospirosis have been hampered because virulent leptospires have the capacity for both long-term survival in the environment as well as persistent infection and shedding by wildlife and livestock. Currently available leptospiral vaccines produce short-term immunity and do not provide cross-protection against many of the over 200 different serovars of pathogenic Leptospira (Thiermann, et al., *J. Am. Vet. Med. Assoc.* 184:722, 1984). These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide may confer a degree of serovar-specific protection.

The pathogenesis of leptospirosis is similar to that of other spirochetal diseases, including syphilis (caused by *Treponema pallidum*) and Lyme borreliosis (caused by *Borrelia burgdorferi*). Both syphilis and Lyme borreliosis are characterized by widespread dissemination early in the course of disease, including invasion of the central nervous system. Leptospira share this ability with other pathogenic spirochetes such that meningitis is a common manifestation of leptospirosis. Another shared feature of spirochetal infections is the ability to persist chronically in the host, as manifested in cases of tertiary syphilis, chronic Lyme arthritis and leptospiral colonization of the renal tubule in reservoir hosts.

Attempts to identify leptospiral outer membrane proteins (OMPs), have led to limited success due to such problems as: 1) the techniques used to identify surface-exposed proteins probably involved damage to the fragile leptospiral outer membrane resulting in exposure of subsurface structures; 2) putative surface-exposed proteins that were identified included a 35–36 kD doublet corresponding to Leptospira endoflagella (Kelson, et al., *J. Med. Microbiol.* 26:47, 1988), which are subsurface structures in spirochetes; and 3) use of sodium docecyl sulfate (SDS) which nonselectively solubilizes proteins irrespective of their native cellular location.

Nunes-Edwards, et al. (*Infect. Immun.* 48:492, 1985) introduced the use of radioimmunoprecipitation and cell fractionation schemes based on the use of SDS in an effort to identify leptospiral OMPs. The leptospires used in their radioimmunoprecipitation procedure were subjected to high speed centrifugation (20,000×g) prior to the addition of antibody. Such high centrifugal forces cause mechanical disruption of the leptospiral outer membrane. Niikura, et al. (*Zbl. Bakt. Hyg. A.* 266:453, 1987) immunoprecipitated SDS-solubilized extracts of virulent and avirulent strains of *L. interrogans* serovar copenhageni that had been labeled by lactoperoxidase-catalyzed surface radioiodination. Since both of these studies precipitated a 35–36 kD doublet consistent with leptospiral endoflagella, there was a concern as to whether the other proteins identified might also have a subsurface rather than a surface location.

Jost, et al. (*J. Med. Microbiol.* 27:143) characterized a monoclonal antibody with specificity for a 35 kD proteinase K sensitive antigen which was present in a leptospiral outer envelope preparation. However, to demonstrate binding of the monoclonal antibody by immunoelectron microscopy, the leptospiral outer membrane had to be disrupted. Doherty, et al. (*J. Med. Microbiol.* 28:143) cloned two leptospiral proteins represented in an SDS-generated outer membrane preparation of *L. interrogans,* but did not provide corroborating evidence that these proteins are either constituents of the outer membrane or are surface-exposed.

Unsuccessful research on the identification of Leptospira and *T. pallidum* OMPs has shown the importance of taking into account spirochetal outer membrane fragility and the lack of outer membrane selectivity of ionic detergents such as SDS (Cunningham, et al., *J. Bacteriol.* 170:5789, 1988; Penn, et al., *J. Gen. Microbiol.* 131:2349, 1985; Stamm, et al., *Infect. Immun.* 55:2255, 1987). Outer membrane proteins are of great importance because they play a key role in bacterial pathogenesis. The identification of outer membrane proteins involved in Leptospira pathogenesis is significant to understanding not only leptospiral outer membrane proteins and their involvement in pathogenesis, but also to understanding other spirochetal outer membrane proteins.

SUMMARY OF THE INVENTION

The present invention is based on the identification of a leptospiral outer membrane protein which is associated with pathogenic strains of Leptospira. The invention describes an approximately 46 kD outer membrane protein, and the gene encoding the protein, originally derived from *L. kirschneri.* The molecular weight was calculated from the deduced amino acid sequence of the polypeptide. The amino acid sequence encodes a membrane lipoprotein with a twenty-five amino acid signal peptide, a lipoprotein signal peptidase cleavage site and an amino terminal cysteine. The deduced 44.1 kD protein has been designated "LipL46" for "lipoprotein from Leptospira" and because the isolated polypeptide migrates, in a denaturing polyacrylamide gel, to a position corresponding to a molecular weight of 46 kD. This immunogenic polypeptide is useful for inducing an immune response to pathogenic spirochetal organisms as well as providing a diagnostic target for spirochetal-associated pathologies.

In a first embodiment, the invention provides a substantially purified LipL46 polypeptide and nucleic acid encoding the LipL46 polypeptide. In accordance with another aspect of the invention, an expression vector containing LipL46 nucleic acid is provided. Also included is a method for producing the LipL46 polypeptide.

The invention further provides a pharmaceutical composition useful for inducing an immune response to a pathogenic spirochete in a subject containing an immunologically effective amount of LipL46 in a pharmaceutically acceptable carrier.

In another aspect, the invention provides a pharmaceutical composition useful for providing immunity to a pathogenic spirochete in a subject comprising an immunogenically effective amount of antibody which binds LipL46 in a pharmaceutically acceptable carrier.

In yet another aspect, the invention provides a method for identifying a compound which binds to LipL46 polypeptide that includes incubating components comprising the compound and LipL46 polypeptide under conditions sufficient to allow the components to interact and measuring the binding of the compound to LipL46 polypeptide.

The invention further provides a method of detecting pathogenic spirochete in a sample which includes contacting a sample suspected of containing a pathogenic spirochete with a reagent that binds to the spirochete-specific cell component and detecting binding of the reagent to the component. In one aspect, the reagent that binds to the spirochete-specific cell component is an oligonucleotide probe for the identification of LipL46 nucleic acid. In another aspect, the reagent that binds to the spirochete-specific cell component is an antibody.

In another aspect, the invention provides a method for detecting antibody to LipL46 polypeptide in a sample including contacting the sample with LipL46 polypeptide, or fragments thereof, under conditions which allow the antibody to bind to LipL46 polypeptide and detecting the binding of the antibody to the LipL46 polypeptide.

In yet another aspect, the invention provides a kit useful for the detection of LipL46 polypeptide, nucleic acid encoding LipL46 and antibodies that bind to LipL46.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIGS. 1A–1C shows a nucleic acid sequence for the lipL46 gene (SEQ ID NO:1) and the deduced amino acid sequence of the LipL46 polypeptide (SEQ ID NO:2).

DETAILED DESCRIPTION OF THE INVENTION

Figure 2:
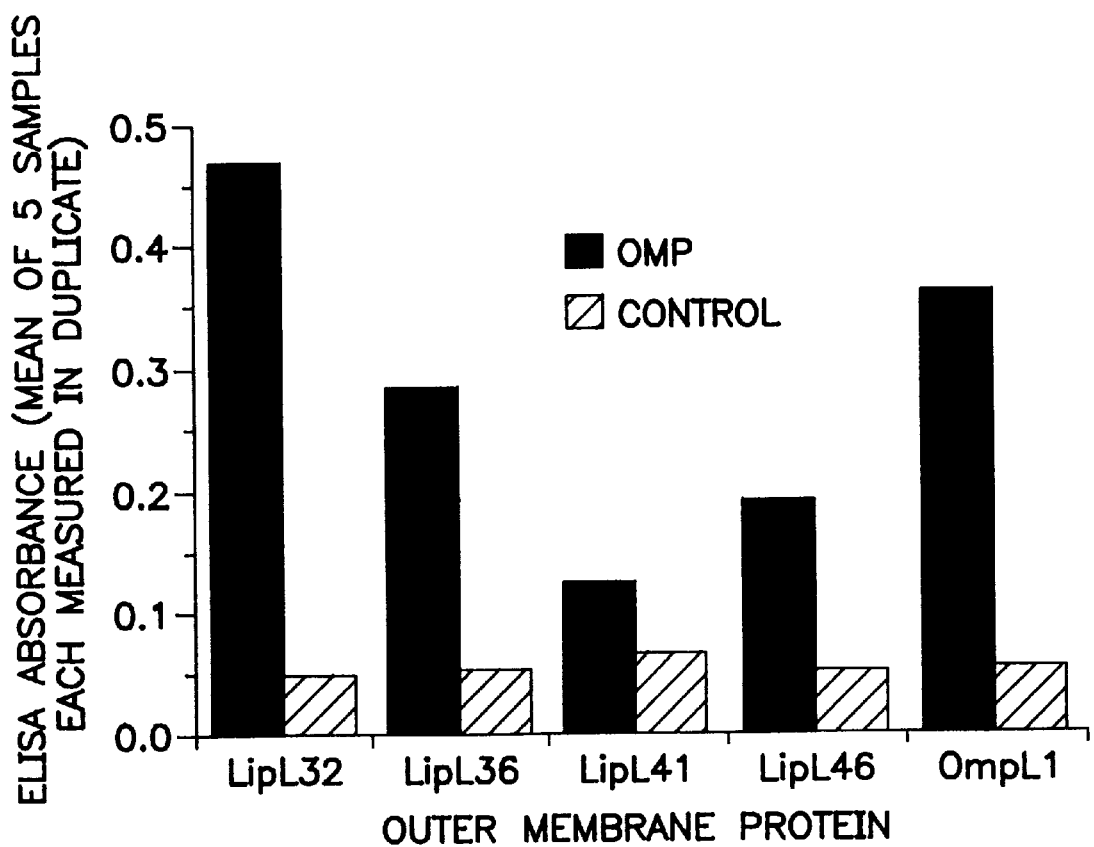
FIG. 2 is a bar graph showing detection of antibodies to LipL32, LipL36, LipL41, LipL46 and OmpL1 in human sera by enzyme-linked immunosorbant assay (ELISA).

The present invention originated from studies on leptospiral outer membrane proteins. The invention provides an immunogenic polypeptide originally isolated from an outer membrane protein of a pathogenic Leptospira species. Also included is a nucleic acid sequence which encodes the polypeptide. The outer membrane protein is a predicted 44.1 kD protein isolated from *Leptospira kirschneri,* which has been termed "LipL46", and is a pathogen-associated exported protein of Leptospira. This immunogenic polypeptide is useful in a pharmaceutical composition for inducing an immune response to pathogenic spirochetes.

LipL46 nucleic acid, polypeptides, host cells and vectors

In a preferred embodiment, the invention provides an isolated polynucleotide sequence encoding a LipL46 polypeptide. An exemplary LipL46 polypeptide of the invention has an amino acid sequence as set forth in SEQ ID NO:2. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode LipL46. It is understood that all polynucleotides encoding all or a portion of LipL46 are also included herein, as long as they encode a polypeptide with LipL46 activity (e.g., provide an antigenic determinant for Leptospira or other pathogenic spirochetes). Such polynucleotides include naturally occurring, synthetic, and intentionally manipulated polynucleotides. For example, LipL46 polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of LipL46 polypeptide encoded by the nucleotide sequence is functionally unchanged. Also included are nucleotide sequences which encode LipL46 polypeptide, such as SEQ ID NO:1. In addition, the invention also includes a polynucleotide encoding a polypeptide having the biological activity of an amino acid sequence of SEQ ID NO:2 and having at least one epitope for an antibody immunoreactive with LipL46 polypeptide. Assays provided herein which show association between leptospiral infection and expression of LipL46 can be used to detect the presence LipL46.

The invention includes polypeptides having substantially the same amino acid sequence as set forth in SEQ ID NO:2 or functional fragments thereof, or amino acid sequences that are substantially identical to SEQ ID NO:2. By "substantially the same" or "substantially identical" is meant a polypeptide or nucleic acid exhibiting at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably identical at the amino acid level to SEQ ID NO:2.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

By a "substantially pure polypeptide" is meant an LipL46 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, LipL46 polypeptide. A substantially pure LipL46 polypeptide may be obtained, for example, by extraction from a natural source (e.g., a plant cell); by expression of a recombinant nucleic acid encoding an LipL46 polypeptide; or by chemically synthesizing the protein. Purity can be measured by any appropriate method, e.g., those described in column chromatography, polyacrylamide gel electrophoresis, or by HPLC analysis.

LipL46 polypeptides of the present invention include peptides, or full length protein, that contains substitutions, deletions, or insertions into the protein backbone, that would still leave a 70% homology to the original protein over the corresponding portion. A yet greater degree of departure from homology is allowed if like-amino acids, i.e. conservative amino acid substitutions, do not count as a change in the sequence. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

The polynucleotide encoding LipL46 includes the nucleotide sequence in FIG. 1 (SEQ ID NO:1), as well as nucleic acid sequences complementary to that sequence. When the sequence is RNA, the deoxyribonucleotides A, G, C, and T of SEQ ID NO:1 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 1 (e.g., SEQ ID NO: 2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Specifically disclosed herein is a DNA sequence for LipL46 represented by SEQ ID NO:1. DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences.

In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide compound.

Primers used according to the method of the invention are designed to be "substantially" complementary to each stand of mutant nucleotide sequence to be amplified. Substantially complementary means that the primers must be sufficiently complementary to hybridize with their respective strands under conditions which allow the agent for polymerization to function. In other words, the primers should have sufficient complementarity with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized + and −strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The amplified product may be detected by Southern blot analysis, without using radioactive probes. In such a process, for example, a small sample of DNA containing a very low level of LipL46 nucleotide sequence is amplified, and analyzed via a Southern blotting technique. The use of non-radioactive probes or labels is facilitated by the high level of the amplified signal.

Preferably the LipL46 polynucleotide of the invention is derived from a leptospiral organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate.

This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding LipL46 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the LipL46 polynucleotide sequences may be inserted into a recombinant expression vector. The term "recombinant expression vector" refers to a plasmid, virus or other vehicle known in the art that has been manipulated by insertion or incorporation of the LipL46 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding LipL46 can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the LipL46 coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized to express the LipL46 coding sequence. These include but are not limited to microorganisms such as bacteria transformed with recombinant bacteriophage DNA, plasmid DNA or cosmid DNA expression vectors containing the LipL46 coding sequence; yeast transformed with recombinant yeast expression vectors containing the LipL46 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the LipL46 coding sequence; insect cell systems infected with recombinant virus expression vectors (e.g., baculovirus) containing the LipL46 coding sequence; or animal cell systems infected with recombinant virus expression vectors (e.g., retroviruses, adenovirus, vaccinia virus) containing the LipL46 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., *Methods in Enzymology* 153:516, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted LipL46 coding sequence.

In yeast, a number of vectors containing constitutive or inducible promoters may be used. For a review see, *Current Protocols in Molecular Biology,* Vol. 2, 1988, Ed. Ausubel et al., Greene Publish. Assoc. & Wiley Interscience, Ch. 13; Grant et al., Expression and Secretion Vectors for Yeast, in *Methods in Enzymology,* 153:516, 1987; Glover, 1986, *DNA Cloning,* Vol. II, IRL Press, Wash., D.C., Ch. 3; and Bitter, Heterologous Gene Expression in Yeast, *Methods in Enzymology,* 152:673, 1987; and *The Molecular Biology of the Yeast Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: *DNA Cloning Vol.* 11, *A Practical Approach,* Ed. DM Glover, 1986, IRL Press, Wash., D.C.). Alternatively, vectors may be used which promote integration of foreign DNA sequences into the yeast chromosome.

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., *Current Protocols in Molecular Biology,* Volumes 1 and 2 (1987), with supplements, and Maniatis et al., *Molecular Cloning, a Laboratory Manual,* Cold Spring Harbor Laboratory (1989). Yet other technical references are known and easily accessible to one skilled in the art.

Antibodies that bind to LipL46

In another embodiment, the present invention provides antibodies that bind to LipL46. Such antibodies are useful for research and diagnostic tools in the study of spirochetal infection in general, and specifically the development of more effective anti-leptospiral therapeutics. Such antibodies may be administered alone or contained in a pharmaceutical composition comprising antibodies against LipL46 and other reagents effective as anti-spirochete therapeutics. It is envisioned that antibodies of the invention can be used to detect the presence of an antigenic determinant resulting from a spirochetal-associated pathology in a subject having, or suspected of having, such a pathology.

The term "epitope", as used herein, refers to an antigenic determinant on an antigen, such as a LipL46 polypeptide, to which the paratope of an antibody, such as an LipL46-specific antibody, binds. Antigenic determinants usually consist of chemically active surface groupings of molecules, such as amino acids or sugar side chains, and can have specific three-dimensional structural characteristics, as well as specific charge characteristics.

Antibodies which bind to the LipL46 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

An antibody suitable for binding to LipL46 is specific for at least one portion of an extracellular region of the LipL46 polypeptide, as shown in FIG. 1 (SEQ ID NO:2). For example, one of skill in the art can use the peptides to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera,* in *Immunochemical Protocols* (Manson, ed.), pages 1–5 (Humana Press 1992); Coligan et al., *Production of Polyclonal Antisera in Rabbits, Rats, Mice and Hamsters,* in *Current Protocols in Immunology,* section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., *Antibodies: A Laboratory Manual,* page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG)*, in *Methods in Molecular Biology*, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer* 46:310 (1990), which are hereby incorporated by reference.

Alternatively, a therapeutically useful anti-LipL46 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989), which is hereby incorporated in its entirety by reference. Techniques for producing humanized monoclonal antibodies are described, for example, by Jones et al., *Nature* 321: 522 (1986); Riechmann et al., *Nature* 332: 323 (1988); Verhoeyen et al., *Science* 239: 1534 (1988); Carter et al., *Proc. Nat'l Acad. Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., *Methods: A Companion to Methods in Enzymology*, Vol. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisonhoff et al., *Arch. Biochem. Biophys.* 89:230 (1960); Porter, *Biochem. J* 73:119 (1959); Edelman et al., *Methods in Enzymology*, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology*, Vol. 2, page 97 (1991); Bird et al., *Science* 242:423–426 (1988); Ladner et al., U.S. Pat. No. 4,946,778; Pack et al., *Bio/Technology* 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology,* Vol. 2, page 106 (1991).

When used for immunotherapy, the monoclonal antibodies of the invention that binds to LipL46 may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., Science, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Pharmaceutical compositions for preventing or treating a spirochetal-associated pathology Spirochetal outer membrane proteins may share common antigenic determinants which can be used to immunize a subject against multiple spirochete-associated disease states. For example, challenging a subject with the LipL46 polypeptide (SEQ ID NO:2) may confer protective immunity to other spirochetal disease states, such as Lyme disease, as well as immunity to leptospirosis.

It is envisioned that methods of the present invention can be used to treat spirochetal-associated disease states or, more specifically, Leptospira-associated disease states. Generally, the terms "treating," "treatment," and the like are used herein to mean obtaining a desired pharmacologic and/or physiologic effect. The effect may be prophylactic in terms of completely or partially preventing a spirochete infection or disease (e.g., leptospirosis or Lyme disease) or sign or symptom thereof, and/or may be therapeutic in terms of a partial or complete cure for an infection or disease and/or adverse effect attributable to the infection or disease. "Treating" as used herein covers any treatment of (e.g., complete or partial), or prevention of, an infection or disease in a mammal, particularly a human, and includes:

(a) preventing the disease from occurring in a subject that may be predisposed to the disease, but has not yet been diagnosed as having it;

(b) inhibiting the infection or disease, i.e., arresting its development; or (c) relieving or ameliorating the infection or disease, i.e., cause regression of the infection or disease.

Thus, the invention includes various pharmaceutical compositions useful for ameliorating symptoms attributable to a spirochete infection or, alternatively, for inducing a protective immune response to prevent such an infection. The pharmaceutical compositions according to the invention are prepared by bringing an antibody against LipL46, a peptide or peptide derivative of LipL46, a LipL46 mimetic, or a LipL46-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, antioxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science*, 249: 1527, (1990); Gilman et al. (eds.) (1990), each of which is herein incorporated by reference.

In one embodiment, the invention provides a pharmaceutical composition useful for inducing an immune response to a virulent spirochete in an animal comprising an immunologically effective amount of LipL46 in a pharmaceutically acceptable carrier. "Administering" the pharmaceutical composition of the present invention may be accomplished by any means known to the skilled artisan. By "subject" is meant any mammal, preferably a human. The term "immunogenically effective amount," as used in describing the invention, is meant to denote that amount of Leptospira antigen which is necessary to induce, in an animal, the production of a protective immune response to Leptospira or any other pathogenic spirochete. The LipL46 protein of the invention is particularly useful in sensitizing the immune system of an animal such that, as one result, an immune response is produced which ameliorates the effect of a spirochetal infection.

The LipL46 protein can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

In addition to the inert diluents, such compositions can also include adjuvants, wetting agents, and emulsifying and suspending agents. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from Mycobacterium tuberculosis, as well as substances found in *Corynebacterium parvum, Bordetella pertussis,* and members of the genus Brucella).

The method of the invention also includes slow release antigen delivery systems such as microencapsulation of antigens into liposomes. Such systems have been used as an approach to enhance the immunogenicity of proteins without the use of traditional adjuvants. Liposomes in the blood stream are generally taken up by the liver and spleen, and are easily phagocytosed by macrophages. Liposomes also allow co-entrapment of immunomodulatory molecules along with the antigens, so that such molecules may be delivered to the site of antigen encounter, allowing modulation of the immune system towards protective responses.

Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Leptospira is desirable include humans, dogs, cattle, horses, deer, mice, goats, wolves and sheep.

Generally, the dosage of LipL46 protein administered to a subject will vary depending on such factors as age, condition, sex and extent of disease, if any, and other variables which can be adjusted by one of ordinary skill in the art.

In another embodiment, the invention provides a method for identifying a compound which binds to LipL46. The method includes incubating components comprising the compound and LipL46 under conditions sufficient to allow the components to interact and measuring the binding of the compound to LipL46. Compounds that bind to LipL46 include peptides, peptidomimetics, polypeptides, chemical compounds and biologic agents as described above.

Incubating includes conditions which allow contact between the test compound and LipL46. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Natl. Acad. Sci. USA,*

80:278, 1983), oligonucleotide ligation assays (OLAs) (Landegren, et al., *Science,* 241:1077, 1988), and the like. Molecular techniques for DNA analysis have been reviewed (Landegren, et al., *Science,* 242:229–237, 1988).

In addition to generating antibodies which bind to antigenic epitopes of LipL46, it is further envisioned that the method of the invention can be used to induce cellular responses, particularly cytotoxic T-lymphocytes (CTLs), to antigenic epitopes of LipL46. Typically, unmodified soluble proteins fail to prime major histocompatibility complex (MHC) class I-restricted CTL responses whereas particulate proteins are extremely immunogenic and have been shown to prime CTL responses in vivo. CTL epitopes and helper epitopes have been identified in proteins from many infectious pathogens. Further, these epitopes can be produced concurrently such that multiple epitopes can be delivered in a form that can prime MHC class I restricted CTL responses. An example of a system that can produce recombinant protein particles carrying one or more epitopes entails the use of the p1 protein of the retrotransposon Tyl of *Saccharomyces cerevisiae* (Adams, et al., *Nature,* 329:68, 1987). Sequences encoding CTL epitopes can, for example, be fused to the C-terminus of p1 and the resulting Ty virus-like particles (Ty-VLPs) may be able to generate a CTL response.

Thus, conserved regions of spirochetal antigens can be identified and incorporated together in a particle which enables the host immune system to mount an effective immune response against multiple spirochetal organisms. Further, the method of the invention can be used to generate particles with multiple epitopes to a single protein, such as LipL46, or multiple epitopes from various spirochetal proteins.

Also included in the screening method of the invention are combinatorial chemistry methods for identifying chemical compounds that bind to LipL46. See, for example, Plunkett and Ellman, *"Combinatorial Chemistry and New Drugs", Scientific American,* April, p.69, (1997).

Detection of LipL46 in vivo and in vitro

In a further embodiment, the invention provides a method of detecting LipL46 in a sample or detecting Leptospira-associated disorder in a subject comprising contacting a cell component containing LipL46 with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe (e.g., ELISA as in Example 3; FIG. 2). The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for LipL46 may be used to detect the presence of LipL46 polypeptide (using antibody) or polynucleotide (using nucleic acid probe) in biological fluids or tissues. Any specimen containing a detectable amount of LipL46 antigen or polynucleotide can be used. A preferred specimen of this invention is blood, urine, cerebrospinal fluid, synovial fluid or tissue of endothelial origin.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

Alternatively, LipL46 polypeptide can be used to detect antibodies to LipL46 polypeptide in a specimen. The LipL46 of the invention is particularly suited for use in immunoassays in which it can be utilized in liquid phase or bound to a solid phase carrier. In addition, LipL46 used in these assays can be detectably labeled in various ways.

Examples of immunoassays which can utilize the LipL46 of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the LipL46 of the invention can be done utilizing immunoassays which run in either the forward, reverse, or simultaneous modes, including immunohistochemical assays on physiological samples. The concentration of LipL46 which is used will vary depending on the type of immunoassay and nature of the detectable label which is used. However, regardless of the type of immunoassay which is used, the concentration of LipL46 utilized can be readily determined by one of ordinary skill in the art using routine experimentation.

The LipL46 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding LipL46 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to LipL46 of the invention may be present in various biological fluids and tissues. Any sample containing a detectable amount of antibodies to LipL46 can be used. Typically, a sample is a liquid such as urine, saliva, cerebrospinal fluid, blood, serum and the like, or a solid or semi-solid such as tissue, feces and the like. Preferably, the sample is serum from the patient.

The monoclonal antibodies of the invention, directed toward LipL46, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of Leptospira LipL46 antigen for which the monoclonal antibodies are specific.

The concentration of detectably labeled monoclonal antibody which is administered should be sufficient such that the binding to those cells, body fluid, or tissue having LipL46 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the subject. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of Leptospira-associated disorder. Thus, by measuring the increase or decrease of Leptospira LipL46 polypeptide or antibodies to LipL46 polypeptide present in various body fluids or tissues, it would be possible to determine whether a particular therapeutic regiment aimed at ameliorating the disorder is effective.

In another embodiment, nucleic acid probes can be used to identify LipL46 nucleic acid from a specimen obtained from a subject suspected of containing a pathogenic Leptospira. Examples of specimens from which nucleic acid sequence encoding LipL46 can be derived because of leptospiral infection include human, swine, porcine, feline, canine, equine, murine, cervine, caprine, lupine, leporidine and bovine species. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

In an embodiment of the invention, purified nucleic acid fragments containing intervening sequences or oligonucleotide sequences of 10–50 base pairs are radioactively labeled. The labeled preparations are used to probe nucleic acid from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an subject having or predisposed to having increased muscle mass.

For the most part, the probe will be detectably labeled with an atom or inorganic radical, most commonly using radionuclides, but also heavy metals can be used. Conveniently, a radioactive label may be employed. Radioactive labels include $^{32}$P, $^{125}$I, $^{3}$H, $^{14}$C, $^{111}$In, $^{99m}$Tc, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}$P-dNTP or terminal phosphate hydrolysis with alkaline phosphatase followed by labeling with radioactive $^{32}$P employing $^{32}$P-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}$P phosphate, or $^{14}$C organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a specimen can be cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washes, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washes may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kD), polyvinylpyrrolidone, (about 250–500 kD) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature*, 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

In nucleic acid hybridization reactions, the conditions used to achieve a particular level of stringency will vary, depending on the nature of the nucleic acids being hybridized. For example, the length, degree of complementarity, nucleotide sequence compound (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific fluorescent antibody. Horseradish peroxidase enzyme can be conjugated to the antibody to catalyze a chemiluminescent reaction. Production of light can then be seen on rapid exposure to film.

Kits for detection of LipL46

The materials for use in the method of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a LipL46 binding reagent, such as an antibody or nucleic acid. A second container may further comprise LipL46 polypeptide. The constituents may be present in liquid or lyophilized form, as desired.

One of the container means may comprise a probe which is or can be detectably labeled. Such probe may be an antibody or nucleotide specific for a target protein, or fragments thereof, or a target nucleic acid, or fragment thereof, respectively, wherein the target is indicative, or correlates with, the presence of LipL46. For example, oligonucleotide probes of the present invention can be included in a kit and used for examining the presence of LipL46 nucleic acid, as well as the quantitative (relative) degree of binding of the probe for determining the occurrence of specific strongly binding (hybridizing) sequences, thus indicating the likelihood for an subject having a Leptospira-associated pathology.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the target nucleic acid sequence, such as a LipL46 nucleic acid sequence, this can be accomplished using oligonucleotide(s) that are primers for amplification. These oligonucleotide primers are based upon identification of the flanking regions contiguous with the target nucleotide sequence.

The kit may also include a container containing antibodies which bind to a target protein, or fragments thereof. Thus, it is envisioned that antibodies which bind to LipL46, or fragments thereof, can be included in a kit.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Isolation and Characterization of the lipL46 Gene

The following 20 amino acid sequence of a 24 kD clostripain proteolytic fragment of LipL46 was previously identified (Alves, S. f., *Ph.D. thesis*, University of California, Davis):

AAAQNTEGGTGLQYNSGAND (SEQ ID NO:3)

The following oligonucleotide was designed based upon the partial amino acid sequence of the LipL46 proteolytic fragment:

Oligonucleotide LipL46-2: GCWGCNGCNCARAAYACN-GARGG (SEQ ID NO:4)

In the above oligonucleotide sequence Y represents C or T/U, R represents A or G, W represents A or T/U and N represents A or C or G or T/U.

Southern hybridization studies using oligonucleotide LipL46-2 as a probe revealed binding to a single 2.7 kb band in digests of total genomic *L. kirschneri* serovar grippotyphosa, strain RM52 DNA treated with the restriction enzyme EcoRI. The 2.7 kb fragment was isolated from a Lambda Zap II sub-library #5 of *L. kirschneri* EcoRI DNA fragments.

DNA sequencing revealed that the 2.7 kb fragment encoded two intact open reading frames, ORF1 and the lipL46 gene, and the 5' end of a third open reading frame, ORF3. The TAA stop codon of ORF1 is 70 bp upstream of the lipL46 gene. There are no terminators or promoter elements between ORF1 and the lipL46 gene, indicating that ORF1 and the lipL46 gene are cotranscribed. Analysis of the LipL46 sequence (FIG. 1, SEQ ID NO:1) indicates that it encodes a membrane lipoprotein with a twenty-five amino acid signal peptide, a lipoprotein signal peptidase cleavage site, and an amino-terminal cysteine. The mature protein would be 436 amino acids long, with a predicted molecular weight of 44.1 kD (FIG. 1, SEQ ID NO:2). Immediately following the lipL46 gene there is an inverted repeat which may function as a rho-independent transcription terminator. A search of the GenBank database revealed no significant homologies to either LipL46 or the gene products of ORF1 and ORF3.

EXAMPLE 2

Characterization of LipL46

LipL46 is solubilized by the nonionic detergent Triton X-114 and fractionates in to the Triton X-114 detergent phase. The hydrophobicity of LipL46 is due to the modification of its amino terminal cysteine by fatty acids, which also serve to anchor LipL46 to the cell membrane. LipL46 can be identified by intrinsic labeling of *Leptospira kirschneri* with tritiated palmitate (Shang et al., *Infect. Immun.*, 64:2322, 1996). LipL46 is one of three proteins (OmpL1, LipL41 and LipL46) identified on the leptospiral surface by surface-immunoprecipitation (Haake et al., *Infect. Immun.*, 59:1131, 1991).

EXAMPLE 3

Host Immune Response to LipL46

LipL46 is expressed by virulent Leptospira species during both cultivation and infection of the mammalian host and is identified by the host immune response to leptospirosis. Sera from nine leptospirosis patients were assayed for the presence of a humoral immune response to human leptospirosis infection by measuring the level of antibody to various known leptospiral antigens (FIG. 2). ELISA assays using purified fusion proteins containing a six histidine tag as antigens. The ELISA reactivity of five human sera to LipL32, LipL36, LipL41, LipL46 and OmpL1 fusion proteins was measured in duplicate and compared with reactivity in control wells containing no antigen. As shown in FIG. 2, antibodies to LipL32, LipL36, LipL41, LipL46 and OmpL1 were detected.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

What is claimed is:

1. An isolated polynucleotide encoding an amino acid sequence as set forth in SEQ ID NO:2.

2. An isolated polynucleotide selected from the group consisting of:

a) SEQ ID NO: 1;

b) SEQ ID NO: 1, wherein T can also be U;

c) a nucleic acid sequence complementary to SEQ ID NO: 1; and d) fragments of a), b), or c) that are at least 15 bases in length and that will hybridize to DNA which encodes the polypeptide of SEQ ID NO: 2.

3. An expression vector containing the polynucleotide of claim 1.

4. The expression vector of claim 3, wherein the vector is a plasmid.

5. The expression vector of claim 3, wherein the vector is a viral vector.

6. The polynucleotide of claim 1, wherein the isolated polynucleotide sequence is from *Leptospira kirschneri.*

7. A host cell transformed with an expression vector of claim 3.

8. The host cell of claim 7, wherein the cell is a eukaryotic cell.

9. The host cell of claim 7, wherein the cell is a prokaryotic cell.

10. A method of producing LipL46 polypeptide comprising:

a) transforming a host cell with a polynucleotide of claim 1;

b) expressing the polynucleotide in the host; and c) recovering the LipL46 polypeptide.

11. The method of claim 10, wherein the host cell is a prokaryotic cell.

12. A kit useful for the detection of Lapel nucleic acid, the kit comprising carrier containing one or more containers comprising a first container containing a polynucleotide selected from the group consisting of:

a) SEQ ID NO: 1;

b) SEQ ID NO: 1, wherein T can also be U;

c) a nucleic acid sequence complementary to SEQ ID NO: 1; and d) fragments of a), b), or c) that are at least 15 bases in length and that will hybridize to DNA which encodes the polypeptide of SEQ ID NO: 2.

13. The kit of claim 12, wherein the polynucleotide is a probe.

14. The kit of claim 13, wherein the probe is detectably labeled.

* * * * *

SEQUENCE LISTING

<160> NUMBER OF SEQ ID NOS: 2

<210> SEQ ID NO 1
<211> LENGTH: 1533
<212> TYPE: DNA
<213> ORGANISM: Leptospira sp.
<220> FEATURE:
<221> NAME/KEY: CDS
<222> LOCATION: (78)..(1463)

<400> SEQUENCE: 1

```
tcagtttgta acttatacgt aactccttcc ctctatcttt gtttcaacct tctacggtat      60
tttcaaggag ttataaa atg aaa tca act ttc cta caa agg gct ttg ctt        110
                   Met Lys Ser Thr Phe Leu Gln Arg Ala Leu Leu
                    1               5                  10 tta atc gta agt gcg gcc tta tta ctt tct tct ttt atc aat tgt aaa        158
Leu Ile Val Ser Ala Ala Leu Leu Leu Ser Ser Phe Ile Asn Cys Lys
             15                  20                  25 gaa gac aaa gac gat aac agt atg ttg ttg ctt ctt gct ctc tta tcg        206
Glu Asp Lys Asp Asp Asn Ser Met Leu Leu Leu Leu Ala Leu Leu Ser
         30                  35                  40 gga gga aat agc gac gcc gga gcc gct atc tgc gac ggt gct tcc gtt        254
Gly Gly Asn Ser Asp Ala Gly Ala Ala Ile Cys Asp Gly Ala Ser Val
     45                  50                  55 caa ggt gga aac acg gtt ctt tcg ggt aac ata act tct agt caa aat        302
Gln Gly Gly Asn Thr Val Leu Ser Gly Asn Ile Thr Ser Ser Gln Asn
 60                  65                  70                  75 ctt tcc gcc tac tct tct tct tcg tta agt gga att gtt aga gtt aaa        350
Leu Ser Ala Tyr Ser Ser Ser Ser Leu Ser Gly Ile Val Arg Val Lys
                 80                  85                  90 aat ggc gct act ctt act ttt gaa aga ggt tct gta att ttc gga act        398
Asn Gly Ala Thr Leu Thr Phe Glu Arg Gly Ser Val Ile Phe Gly Thr
             95                 100                 105 gct ggt tcc gct tta atc atc gaa caa gga gga aag atc gtt aca aac        446
Ala Gly Ser Ala Leu Ile Ile Glu Gln Gly Gly Lys Ile Val Thr Asn
        110                 115                 120 gga gac gct gcc gca ccc gta tgc ttt act tct tct aaa gtt tcc gga        494
Gly Asp Ala Ala Ala Pro Val Cys Phe Thr Ser Ser Lys Val Ser Gly
    125                 130                 135 aac aga gcc cca ggc gat tgg ggt ggt atc ttg atc gta gga gac ggt        542
Asn Arg Ala Pro Gly Asp Trp Gly Gly Ile Leu Ile Val Gly Asp Gly
140                 145                 150                 155 att ggt tcc aga gca gcc gca caa aac acg gaa ggt gga acc ggt ctt        590
Ile Gly Ser Arg Ala Ala Ala Gln Asn Thr Glu Gly Gly Thr Gly Leu
                160                 165                 170 caa tac aat agc ggt gcc aat gat aac gga agt tcg ggt aac ctt act        638
Gln Tyr Asn Ser Gly Ala Asn Asp Asn Gly Ser Ser Gly Asn Leu Thr
            175                 180                 185 tat acg atc gtt gaa ttt gcc gga aac gaa gtt tct ccc ggt gac gag        686
Tyr Thr Ile Val Glu Phe Ala Gly Asn Glu Val Ser Pro Gly Asp Glu
        190                 195                 200 tta aac gga ctt tct atg tat gtg gta gga agt ggt act act tta gat        734
Leu Asn Gly Leu Ser Met Tyr Val Val Gly Ser Gly Thr Thr Leu Asp
    205                 210                 215 cac gtt caa gtc cac aga cat ttg gac gac ggt ata gaa gct tgg ggt        782
His Val Gln Val His Arg His Leu Asp Asp Gly Ile Glu Ala Trp Gly
220                 225                 230                 235 ggc gct tgg act ggt aaa tat ctt ttg atg acc ggt gga atg gac gac        830
Gly Ala Trp Thr Gly Lys Tyr Leu Leu Met Thr Gly Gly Met Asp Asp
```

-continued

```
                   240                 245                 250
gat tta gat tta gat gaa gct ttc act gga aaa gtt cag ttc tta atc        878
Asp Leu Asp Leu Asp Glu Ala Phe Thr Gly Lys Val Gln Phe Leu Ile
            255                 260                 265 gct cat aaa tat cct act agt tgt ggt gga acc gca tcc acc gac cca        926
Ala His Lys Tyr Pro Thr Ser Cys Gly Gly Thr Ala Ser Thr Asp Pro
        270                 275                 280 cac ggt ttt gaa atg gac gga act cat agc ggt ggt acc gca tcc gcg        974
His Gly Phe Glu Met Asp Gly Thr His Ser Gly Gly Thr Ala Ser Ala
    285                 290                 295 act tct aaa acg gcc aca aac gta aaa ctt tcc aac ttt act ctt ctt       1022
Thr Ser Lys Thr Ala Thr Asn Val Lys Leu Ser Asn Phe Thr Leu Leu
300                 305                 310                 315 gga aaa agc gtt tcc aac gga ttt gga gca aga ctg aga gaa gga ctt       1070
Gly Lys Ser Val Ser Asn Gly Phe Gly Ala Arg Leu Arg Glu Gly Leu
                320                 325                 330 caa ggt aaa ttt tcg aac gga gcc att tac ggt ttt caa gcc gga aac       1118
Gln Gly Lys Phe Ser Asn Gly Ala Ile Tyr Gly Phe Gln Ala Gly Asn
            335                 340                 345 gtt gat tgt gta gcg aat gca agc gta ggt ggt cca gtg acc tct cct       1166
Val Asp Cys Val Ala Asn Ala Ser Val Gly Gly Pro Val Thr Ser Pro
        350                 355                 360 act ttt gca aac gtc tta gta gaa gct tct aaa gga aac gga aat acc       1214
Thr Phe Ala Asn Val Leu Val Glu Ala Ser Lys Gly Asn Gly Asn Thr
    365                 370                 375 gcg gct tgt tcg tta cct aca aac gga ctt tct tcc act cct gta att       1262
Ala Ala Cys Ser Leu Pro Thr Asn Gly Leu Ser Ser Thr Pro Val Ile
380                 385                 390                 395 tcc tta ggt tct ggg gat tcg gat aac tgc gaa ttt gcg acc aaa ccg       1310
Ser Leu Gly Ser Gly Asp Ser Asp Asn Cys Glu Phe Ala Thr Lys Pro
                400                 405                 410 gat tat caa cct tct gga gaa gcc gcg gct tta gcc ggt tcc gct cta       1358
Asp Tyr Gln Pro Ser Gly Glu Ala Ala Ala Leu Ala Gly Ser Ala Leu
            415                 420                 425 agc gct caa tcc tcg gat tcg ttt ttt acc gat aac acc act tac ggc       1406
Ser Ala Gln Ser Ser Asp Ser Phe Phe Thr Asp Asn Thr Thr Tyr Gly
        430                 435                 440 ggt atg gta aac ggt ttg aac tgg gct ttc ggt tgg acc gtt tat aga       1454
Gly Met Val Asn Gly Leu Asn Trp Ala Phe Gly Trp Thr Val Tyr Arg
    445                 450                 455 gca aga taa acttatacat taggattccc taatttggga atcctaattc               1503
Ala Arg
460 aaaattttaa tctattttaa aatcattaga                                      1533
```

<210> SEQ ID NO 2
<211> LENGTH: 461
<212> TYPE: PRT
<213> ORGANISM: Leptospira sp.

<400> SEQUENCE: 2

```
Met Lys Ser Thr Phe Leu Gln Arg Ala Leu Leu Leu Ile Val Ser Ala
  1               5                  10                  15

Ala Leu Leu Leu Ser Ser Phe Ile Asn Cys Lys Glu Asp Lys Asp Asp
                 20                  25                  30

Asn Ser Met Leu Leu Leu Leu Ala Leu Leu Ser Gly Gly Asn Ser Asp
             35                  40                  45

Ala Gly Ala Ala Ile Cys Asp Gly Ala Ser Val Gln Gly Gly Asn Thr
         50                  55                  60
```

-continued

```
Val Leu Ser Gly Asn Ile Thr Ser Ser Gln Asn Leu Ser Ala Tyr Ser
 65                      70                  75                  80

Ser Ser Ser Leu Ser Gly Ile Val Arg Val Lys Asn Gly Ala Thr Leu
                 85                  90                  95

Thr Phe Glu Arg Gly Ser Val Ile Phe Gly Thr Ala Gly Ser Ala Leu
            100                 105                 110

Ile Ile Glu Gln Gly Gly Lys Ile Val Thr Asn Gly Asp Ala Ala Ala
            115                 120                 125

Pro Val Cys Phe Thr Ser Ser Lys Val Ser Gly Asn Arg Ala Pro Gly
130                 135                 140

Asp Trp Gly Gly Ile Leu Ile Val Gly Asp Gly Ile Gly Ser Arg Ala
145                 150                 155                 160

Ala Ala Gln Asn Thr Glu Gly Gly Thr Gly Leu Gln Tyr Asn Ser Gly
                165                 170                 175

Ala Asn Asp Asn Gly Ser Ser Gly Asn Leu Thr Tyr Thr Ile Val Glu
                180                 185                 190

Phe Ala Gly Asn Glu Val Ser Pro Gly Asp Glu Leu Asn Gly Leu Ser
            195                 200                 205

Met Tyr Val Val Gly Ser Gly Thr Thr Leu Asp His Val Gln Val His
            210                 215                 220

Arg His Leu Asp Asp Gly Ile Glu Ala Trp Gly Gly Ala Trp Thr Gly
225                 230                 235                 240

Lys Tyr Leu Leu Met Thr Gly Gly Met Asp Asp Leu Asp Leu Asp
                245                 250                 255

Glu Ala Phe Thr Gly Lys Val Gln Phe Leu Ile Ala His Lys Tyr Pro
                260                 265                 270

Thr Ser Cys Gly Gly Thr Ala Ser Thr Asp Pro His Gly Phe Glu Met
            275                 280                 285

Asp Gly Thr His Ser Gly Gly Thr Ala Ser Ala Thr Ser Lys Thr Ala
            290                 295                 300

Thr Asn Val Lys Leu Ser Asn Phe Thr Leu Leu Gly Lys Ser Val Ser
305                 310                 315                 320

Asn Gly Phe Gly Ala Arg Leu Arg Glu Gly Leu Gln Gly Lys Phe Ser
                325                 330                 335

Asn Gly Ala Ile Tyr Gly Phe Gln Ala Gly Asn Val Asp Cys Val Ala
                340                 345                 350

Asn Ala Ser Val Gly Gly Pro Val Thr Ser Pro Thr Phe Ala Asn Val
            355                 360                 365

Leu Val Glu Ala Ser Lys Gly Asn Gly Asn Thr Ala Ala Cys Ser Leu
370                 375                 380

Pro Thr Asn Gly Leu Ser Ser Thr Pro Val Ile Ser Leu Gly Ser Gly
385                 390                 395                 400

Asp Ser Asp Asn Cys Glu Phe Ala Thr Lys Pro Asp Tyr Gln Pro Ser
                405                 410                 415

Gly Glu Ala Ala Ala Leu Ala Gly Ser Ala Leu Ser Ala Gln Ser Ser
            420                 425                 430

Asp Ser Phe Phe Thr Asp Asn Thr Thr Tyr Gly Gly Met Val Asn Gly
            435                 440                 445

Leu Asn Trp Ala Phe Gly Trp Thr Val Tyr Arg Ala Arg
450                 455                 460
```